(12) United States Patent
Sykes

(10) Patent No.: US 10,265,740 B2
(45) Date of Patent: Apr. 23, 2019

(54) SOLDER CLEANING SYSTEM

(71) Applicant: XYZTEC BV, Panningen (NL)

(72) Inventor: Robert Sykes, Tendring (GB)

(73) Assignee: XYZTEC BV, Panningen (NL)

( * ) Notice: Subject to any disclaimer, the term of this patent is extended or adjusted under 35 U.S.C. 154(b) by 40 days.

(21) Appl. No.: 15/328,701

(22) PCT Filed: Jul. 17, 2015

(86) PCT No.: PCT/EP2015/066389
§ 371 (c)(1),
(2) Date: Jan. 24, 2017

(87) PCT Pub. No.: WO2016/012357
PCT Pub. Date: Jan. 28, 2016

(65) Prior Publication Data
US 2017/0209903 A1    Jul. 27, 2017

(30) Foreign Application Priority Data

Jul. 25, 2014  (GB) .................... 1413225.2

(51) Int. Cl.
| | |
|---|---|
| *B23K 37/00* | (2006.01) |
| *B08B 5/02* | (2006.01) |
| *B23K 3/02* | (2006.01) |
| *B23K 1/018* | (2006.01) |
| *B08B 7/00* | (2006.01) |
| *G01N 19/04* | (2006.01) |

(52) U.S. Cl.
CPC .............. *B08B 5/02* (2013.01); *B08B 7/0071* (2013.01); *B23K 1/018* (2013.01); *B23K 3/028* (2013.01); *B23K 3/029* (2013.01); *G01N 19/04* (2013.01); *G01N 2203/0296* (2013.01)

(58) Field of Classification Search
CPC ........ B08B 5/02; B08B 7/0071; G01N 19/04; G01N 2203/0296; B23K 1/018; B23K 3/028; B23K 3/029
USPC ......... 228/102–104, 119, 191, 264, 19–20.5, 228/8–11, 13
See application file for complete search history.

(56) References Cited

U.S. PATENT DOCUMENTS

| | | | |
|---|---|---|---|
| 3,773,261 A | 11/1973 | Helton | |
| 4,022,370 A * | 5/1977 | Durney | B23K 1/018 219/85.12 |

(Continued)

FOREIGN PATENT DOCUMENTS

| | | | | |
|---|---|---|---|---|
| DE | 24 40 005 A1 | 2/1975 | | |
| DE | 2440005 | * | 2/1975 | ........... B23K 3/0338 |

(Continued)

OTHER PUBLICATIONS

English Machine Translation for DE2440005.*
EPO International Search Report for PCT/EP2015/066389 dated Sep. 23, 2015.

*Primary Examiner* — Kiley S Stoner
(74) *Attorney, Agent, or Firm* — Shumaker, Loop & Kendrick, LLP

(57) ABSTRACT

A method of cleaning solder from the jaws of a solder ball test device including the steps of heating a gas to a temperature above the melting temperature of the solder and directing the heated has over the jaws of a solder ball test device to remove solder from the jaws, and an apparatus for carrying out the method.

7 Claims, 2 Drawing Sheets

(56) References Cited

U.S. PATENT DOCUMENTS

| | | | | |
|---|---|---|---|---|
| 4,136,444 | A * | 1/1979 | Durney | H05K 13/0486 219/230 |
| 4,625,355 | A * | 12/1986 | Miyashita | B23K 3/028 15/104.04 |
| 5,969,262 | A * | 10/1999 | Ino | G01N 3/00 73/827 |
| 6,237,422 | B1 * | 5/2001 | Sykes | G01N 3/04 73/827 |
| 6,273,317 | B1 * | 8/2001 | Arai | B23K 1/085 228/33 |
| 6,685,080 | B1 * | 2/2004 | Kee | B23K 1/018 228/102 |
| 7,617,962 | B2 * | 11/2009 | Kajii | B23K 1/206 118/204 |
| 2002/0033409 | A1 * | 3/2002 | Cilia | B23K 1/018 228/19 |
| 2002/0042960 | A1 * | 4/2002 | Hayashi | B08B 1/04 15/93.1 |
| 2002/0121149 | A1 * | 9/2002 | Lee | G01N 3/24 73/865.9 |
| 2004/0099709 | A1 * | 5/2004 | Chin | B23K 1/018 228/13 |
| 2006/0231834 | A1 * | 10/2006 | Yeh | G01N 3/00 257/48 |
| 2008/0212067 | A1 * | 9/2008 | Gupta | B23K 31/02 356/35.5 |
| 2008/0313879 | A1 * | 12/2008 | Jadhav | G01N 3/00 29/557 |
| 2009/0019941 | A1 * | 1/2009 | Sykes | G01N 3/00 73/826 |
| 2009/0056469 | A1 * | 3/2009 | Sykes | G01N 3/24 73/827 |
| 2009/0139303 | A1 * | 6/2009 | Zhang | G01N 3/00 73/12.09 |
| 2009/0301216 | A1 * | 12/2009 | Sykes | G01N 3/00 73/833 |
| 2011/0127316 | A1 * | 6/2011 | Dunlop | B08B 7/0071 228/176 |
| 2011/0214510 | A1 * | 9/2011 | Lilley | G01N 3/24 73/841 |
| 2013/0099811 | A1 * | 4/2013 | Lee | G01R 1/06722 324/754.11 |
| 2013/0314117 | A1 * | 11/2013 | Gardell | G01R 31/048 324/755.01 |

FOREIGN PATENT DOCUMENTS

| | | | | |
|---|---|---|---|---|
| EP | | 635 329 A1 | 1/1995 | |
| EP | | 2 386 846 A1 | 11/2011 | |
| WO | WO-2005093436 A2 * | | 10/2005 | G01N 3/00 |

* cited by examiner

SOLDER CLEANING SYSTEM

BACKGROUND OF THE INVENTION

Electrical connections in semiconductor and electronic components are often made using a protrusion or "ball" of conducting solder, such balls are well known in the industry. They are typically bonded to a pad on a component or Silicone Chip or Silicone Wafer, again these being well known to those experienced in the art. Currently the diameter of the balls ranges from 1 mm to 0.040 mm but future sizes are expected to follow the established trend and become still smaller. The balls are also commonly arranged to be adjacent to each other in the form of complete or partial two dimensional matrixes. The pitch between balls varies but is in the order of two times their diameter. Such balls are often tested by gripping them with a pair of special tweezers and then pulling them to test the strength of their bond to the pad. Such tweezers are usually connected to a load cell and the quality of the bond can then be graded by the force to failure.

To test the bond it is desirable to grip the ball so that the highest possible pull force can be exerted on to the bond. Prior art exists for this using a cavity in each of the opposing jaws of the tweezers that reforms the ball as the jaws close around it. This system is known as CBP, standing for "Cold Ball Pull" or "Cold Bump Pull".

A problem exists where during repeated use the cavity of the jaws starts to build up with solder. The shape of the cavity is very important and the build-up of solder adversely affects the test performance by reducing the maximum force that can be exerted on to the bond. Because of their small size, cleaning the solder out of the cavities is very difficult. Mechanically cleaning them requires very small tools and very precise alignment of the cleaning tool to the cavity. Such cleaning methods are time consuming and can damage the cavities. This invention provides a means to easily clean the build-up of solder out of the cavities.

BRIEF SUMMARY OF THE INVENTION

According to a first aspect of the present invention there is provided a method of cleaning solder from the jaws of a solder ball test device, the method comprising the steps of:
heating a gas to a temperature above the melting temperature of the solder; and
directing the heated gas over the jaws of a solder ball test device to remove solder from said jaws.

The gas is heated to a temperature sufficient to melt the solder. It will be appreciated that the temperature to which the gas is heated is below the melting temperature of the material of the jaws. The velocity of the heated gas exiting the nozzle assists in the removal of solder from the jaws.

The step of heating the gas may comprises the steps of:
providing heat exchanger having an internal volume and an outlet nozzle in fluid communication with said internal volume;
supplying a gas under pressure to said internal volume; and
operating the heat exchanger to heat said pressurised gas such that heated gas is delivered through the outlet nozzle.

The heat exchanger may include an electrical heater cartridge. The outlet nozzle may has a typical bore diameter of between 0.5 mm and 1.5 mm. The pressure of the heated gas at the exit from the nozzle may be in the region of 2 to 5 bar. The gas may be heated to a typical temperature of between 200 degrees Centigrade and 500 degrees Centigrade.

The method may further include the step of moving the jaws in the heated gas.

According to a further aspect of the present invention there is provided an apparatus for cleaning solder from the jaws of a solder ball test device, the apparatus including a heat exchanger and a body enclosing the heat exchanger such that a volume is enclosed between the body and the heat exchanger, the apparatus further including an inlet to the volume and an outlet nozzle in fluid communication with said volume wherein, in use, gas under pressure introduced to the volume is heated by the heat exchanger such that heated gas is delivered through the nozzle.

The heat exchanger may include an electrical heater cartridge. The outlet nozzle may have a typical bore diameter of between 0.5 mm and 1.5 mm. The pressure of the heated gas at the exit from the nozzle may be in the region of 2 to 5 bar. The gas may be heated to a typical temperature of between 200 degrees Centigrade and 500 degrees Centigrade.

The apparatus may further include a temperature sensor. The apparatus may further include a heat guard to protect users of the apparatus. The heat guard may include a box to receive molten solder released from the jaws by the heated gas.

BRIEF DESCRIPTION OF THE DRAWINGS

Features of the invention will be apparent from the following description of a preferred embodiment described with reference to the accompanying drawings in which.

DETAILED DESCRIPTION OF THE INVENTION

Figure 1:
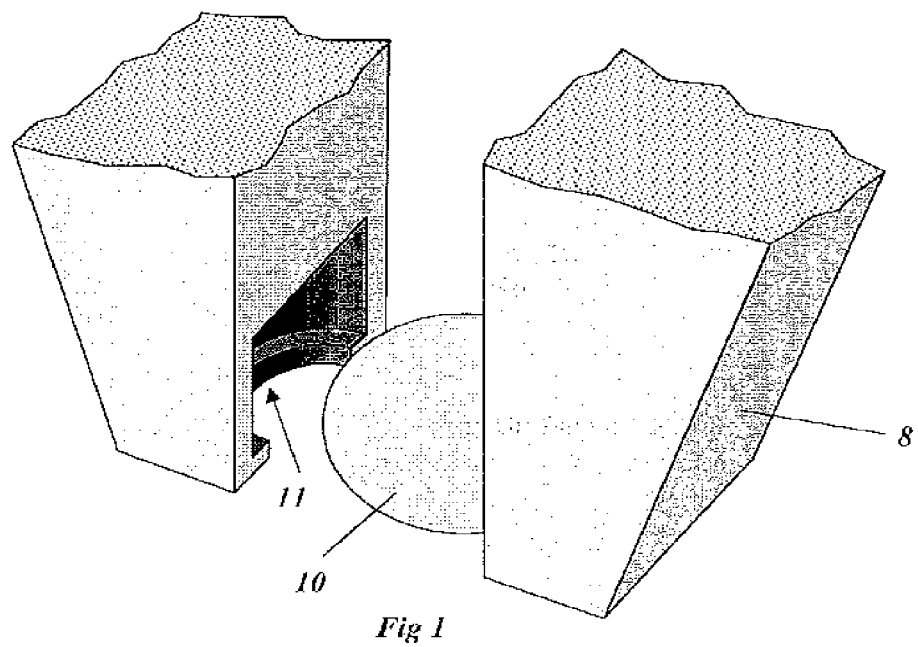
FIG. 1 shows a schematic representation of a typical solder ball ready to be tested before it has been gripped by the jaws.

FIG. 1 illustrates typical jaws 8 of a solder ball test device. Each jaw 8 includes a cavity 11 that close around a solder ball 10 and reform it to the cavity shape. This reforming of the solder ball 10 enables the optimum grip.

Figure 2:
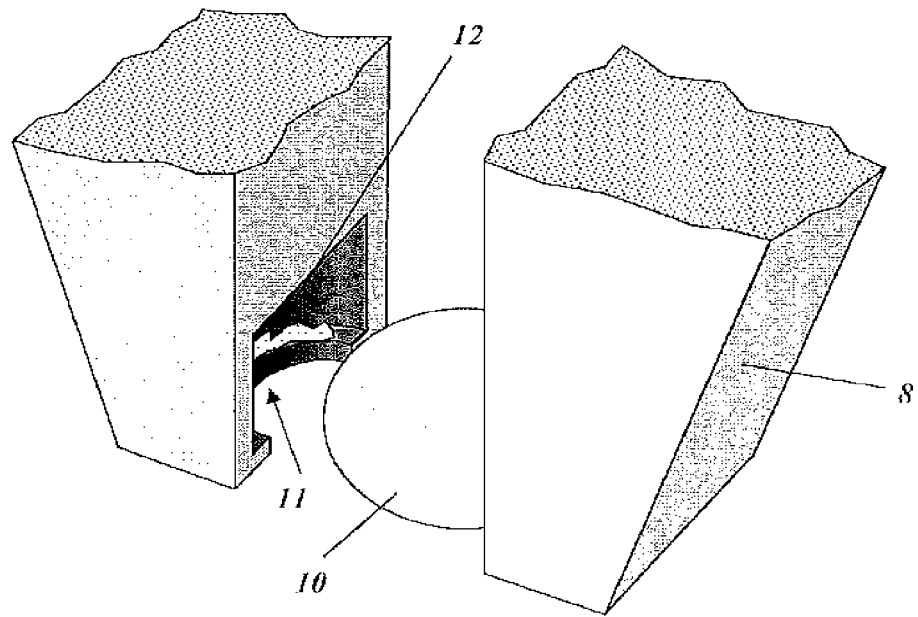
FIG. 2 shows a schematic representation similar to FIG. 1 but where the jaws have a build-up of solder in the cavity.

FIG. 2 illustrates a similar pair of jaws 8 with a build-up of solder 12 within the cavity 11 that affects the reforming of the solder ball 10, reducing the maximum possible pull force.

Figure 3:
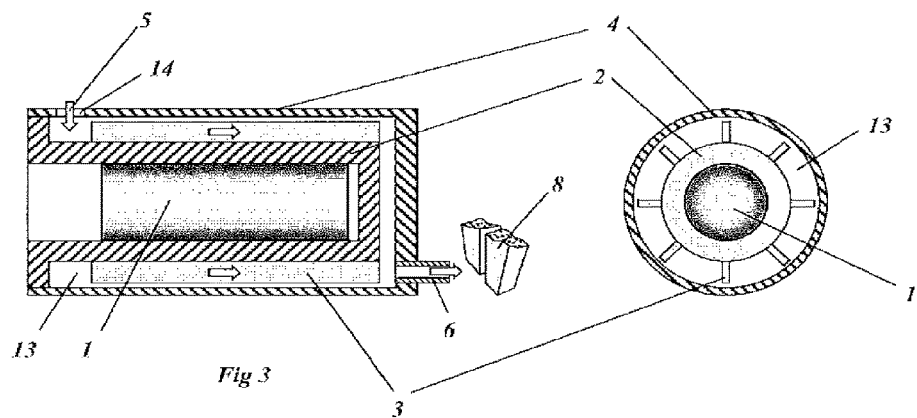
FIG. 3 shows schematic representation of a cleaning system that removes the build-up of solder from the jaws.

FIG. 3 illustrates a schematic representation of one embodiment of the invention. A heater 1 is located in a heat exchanger 2 and is used to raise the temperature of the heat exchanger 2 to a value above the melting point of the solder ball 10. The melting temperature of solders varies between around 150° C. to 250° C. The heat exchanger 2 would typically be raised to a temperature of between 200° C. to 500° C. It is important that the materials used in the construction of the invention can withstand the temperatures that they will be exposed to. The heat exchanger 2 can, for example, be a plain cylinder but in a preferred embodiment it would have fins 3 to increase its surface area. The heat exchanger 2 is enclosed in a body or casing 4 such that air, or any other gas 5, can be pumped into a volume 13 enclosed between the body 4 and the heat exchanger 2.

Figure 4:
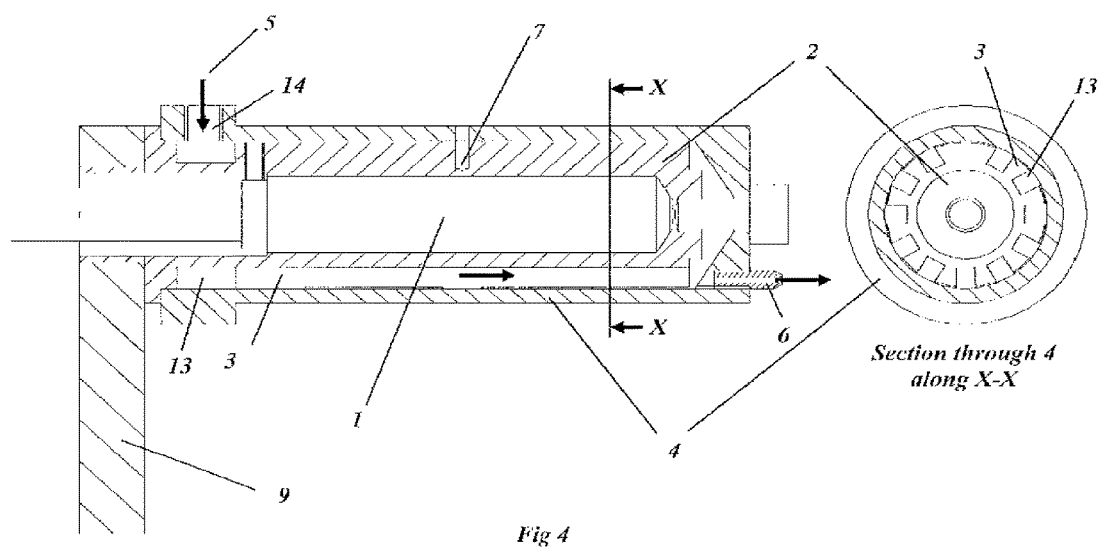
FIG. 4 shows a representation similar to FIG. 3 in more detail of a preferred embodiment.

FIG. 4 illustrates a round cylindrical design mounted upon a support 9. Other embodiments of the invention may be based on square cylinders, rectangular cylinders or flat heat exchangers with the fins and or heat exchange surface on only one or more sides.

Under the pressure generated by a pump, a pressurised storage cylinder or other such means, gas flows into the volume 13 through an inlet 14 and over the heat exchanger 2. The temperature of the gas 5 is raised above that of the melting point of solder. The heated gas 5 then exits out of a nozzle 6 of the body 4. The gas exiting out of the nozzle is subsequently used to melt the solder in the cavities 11 of the jaws 8. The velocity of the gas 5 assists in moving the melted solder out of the cavities and away from the jaws 8.

The jaws 8 to be cleaned are only slightly larger than the solder balls 10, typically less than 1 mm. To melt the solder in the cavities 11 the diameter of the heated gas jet does not need to be large; the nozzle 6 bore diameter may typically be between 0.5 to 1.5 mm. The jet though does need to have a relatively high velocity. The total pressure at exit from the nozzle 6 may thus be in the region of 2 to 5 bar.

In a preferred embodiment, the heater 1 is an electrical heater cartridge with its temperature being controlled by a temperature sensor placed in close proximity to it; for example in a hole or aperture 7 extending through the body 4 and into the heat exchanger 2.

In preferred embodiments, the heat exchanger 2 is made from a material with a relatively high heat conductivity whereas the body 4 and support 9 would be preferably, but not exclusively, be made from a material with lower heat conductivity. In a preferred embodiment the assembly would be mounted within a heat guard to protect operators from the hot gas and components. The guard would have a hole in it allowing the jaws 8 to be placed into the hot gas jet for cleaning. The guard may also include a box that the molten solder removed from the jaws 8 is captured in for safe disposal.

Effective cleaning of the cavities 11 requires the jaws 8 to be moved and rotated in the hot gas jet. This can be done manually or by mounting the cleaning system on the same machine that the jaws 8 are used on thereby providing an automatic cleaning station.

The invention claimed is:

1. An automatic cleaning station for cleaning solder from jaws of a solder ball test device, the cleaning station comprising a cleaning system, and the cleaning system comprising:
   a heat exchanger and a body enclosing the heat exchanger such that a volume is enclosed between the body and the heat exchanger; and
   an inlet to the volume and an outlet nozzle in fluid communication with the volume;
   wherein, in use, gas under pressure introduced to the volume is heated by the heat exchanger such that heated gas is delivered through the nozzle;
   wherein the automatic cleaning station is mounted on the solder ball test device; and
   wherein the solder ball test device is configured to move and to rotate the jaws in the heated gas.

2. The automatic cleaning station according to claim 1, wherein the heat exchanger comprises an electrical heater cartridge.

3. The automatic cleaning station according to claim 1, wherein the outlet nozzle has a bore diameter between 0.5 mm and 1.5 mm.

4. The automatic cleaning station according to claim 1, wherein the pressure of the heated gas at an exit from the nozzle is between 2 and 5 bar.

5. The automatic cleaning station according to claim 1, wherein the heat exchanger is adapted to heat the gas to a temperature between 200 degrees Centigrade and 500 degrees Centigrade.

6. The automatic cleaning station according to claim 1, further comprising a temperature sensor.

7. The automatic cleaning station according to claim 1, further comprising a heat guard adapted to protect a user.

* * * * *